United States Patent [19]

Engelson

[11] Patent Number: 5,599,492
[45] Date of Patent: Feb. 4, 1997

[54] METHOD FOR MAKING A GUIDEWIRE WITH A FLEXIBLE DISTAL TIP

[75] Inventor: Erik T. Engelson, Mountain View, Calif.

[73] Assignee: Target Therapeutics, Inc., Fremont, Calif.

[21] Appl. No.: 357,975

[22] Filed: Dec. 16, 1994

Related U.S. Application Data

[63] Continuation of Ser. No. 50,718, Apr. 19, 1993, abandoned, which is a continuation of Ser. No. 791,967, Nov. 13, 1991, abandoned, which is a division of Ser. No. 495,567, Mar. 19, 1990, Pat. No. 5,095,915.

[51] Int. Cl.⁶ .................... B29C 47/02; B29C 47/18
[52] U.S. Cl. .............. 264/167; 264/171.17; 264/209.2; 264/209.3; 264/230; 264/301
[58] Field of Search .................... 264/149, 167, 264/230, 301, 305, 23, 171.14, 171.17, 209.2, 209.3; 128/657, 772; 604/282, 170; 156/85, 86, 293

[56] References Cited

U.S. PATENT DOCUMENTS

| | | |
|---|---|---|
| 1,035,931 | 7/1912 | Woodhouse . |
| 1,813,039 | 3/1930 | Escol . |
| 2,248,934 | 7/1941 | Auzin ........................ 264/305 |
| 2,437,542 | 3/1948 | Krippendorf . |
| 3,789,841 | 2/1974 | Antoshkiw . |
| 3,832,253 | 8/1974 | Di Palma et al. .............. 156/86 |
| 3,928,519 | 12/1975 | Kashiyama et al. . |
| 3,973,556 | 7/1976 | Fleischhacker et al. . |
| 4,079,757 | 3/1978 | Fischer et al. . |
| 4,251,305 | 2/1981 | Becker et al. ................ 156/86 |
| 4,403,985 | 9/1983 | Boretos . |
| 4,545,390 | 10/1985 | Leary . |
| 4,619,274 | 10/1986 | Morrison . |
| 4,636,346 | 1/1987 | Gold et al. ................ 264/149 |
| 4,655,746 | 4/1987 | Daniels et al. . |
| 4,690,175 | 9/1987 | Ouchi et al. . |
| 4,732,163 | 3/1988 | Bonello et al. . |
| 4,739,768 | 4/1988 | Engelson ................ 604/282 |
| 4,748,986 | 6/1988 | Morrison et al. . |
| 4,753,765 | 6/1988 | Pande ........................ 264/167 |
| 4,813,934 | 3/1989 | Engelson et al. . |
| 4,874,373 | 10/1989 | Luther et al. ............ 264/301 |
| 4,941,473 | 7/1990 | Tenerz et al. . |
| 4,955,862 | 9/1990 | Sepetka . |
| 5,171,383 | 12/1992 | Sagaye et al. ............ 604/282 |

FOREIGN PATENT DOCUMENTS 2247262  9/1975  France .

*Primary Examiner*—Mathieu D. Vargot
*Attorney, Agent, or Firm*—Morrison & Foerster

[57] ABSTRACT

A method for producing catheter guidewire composed of a wire core whose distal end section is encased in a polymer sleeve, to increase the column strength of the core. Axially spaced grooves formed in the sleeve increase the flexibility of the core end section. The guidewire is advantageous for use with a small-diameter catheter in accessing body sites along a tortuous vessel pathway.

3 Claims, 3 Drawing Sheets

METHOD FOR MAKING A GUIDEWIRE WITH A FLEXIBLE DISTAL TIP

This application is a continuation of application Ser. No. 08/050,718, filed Apr. 19, 1993 now abandoned, which is a continuation of Ser. No. 07/791,967, filed Nov. 13, 1991, now abandoned, which is a divisional of Ser. No. 07/495,567, filed Mar. 19, 1990, now U.S. Pat. No. 5,095,915.

TECHNICAL FIELD

The present invention relates to a catheter guidewire, and in particular, to a guidewire having a flexible distal tip, and to a method of making the guidewire.

BACKGROUND OF THE INVENTION

Catheters are being used increasingly as a means for delivering diagnostic or therapeutic agents to internal target sites that can be accessed through the circulatory system. Often the site which one wishes to access by catheter is buried within a soft tissue, such as brain or liver, and is only reached by a tortuous route through small vessels or ducts—typically less than about 3 mm lumen diameter—in the tissue.

In one general method for accessing a deep-organ target site along a tortuous-path vessel, a torqueable guide wire and catheter are directed as a unit from a body access site to a tissue region containing a target site. The guide wire is bent at its distal end and may be guided by alternately rotating and advancing the wire along a tortuous, small-vessel pathway, to the target site. Typically the guide wire and catheter are advanced by alternately advancing the wire along a region of the pathway, then advancing the catheter axially over the advanced wire portion.

The difficulty in accessing such target body regions is that the catheter and guidewire must be quite flexible in order to follow the tortuous path into the tissue, and at the same time, stiff enough to allow the distal end of the catheter to be manipulated from an external access site, which may be as much as a meter or more from the tissue site.

Heretofore, catheter guidewires for use in guiding a catheter along a tortuous path have employed a variable-flexibility construction in which the distal end section of the wire is tapered along its length to allow greater flexibility at the wire's distal end region, where the sharpest wire turns are encountered. The tapered section of the wire is encased in a wire coil, such as a platinum coil, to increase the column strength of the tapered wire section without significant loss of flexibility in this region. Such guide wire constructions are disclosed, for example, in U.S. Pat. Nos. 3,789,841, 4,545,390, and 4,619,274.

The tapered guidewire construction just described is prepared, typically, by forming a fine-wire coil, cutting the coil to a desired length, and fastening the coil to the tapered distal end section of the guidewire, typically by soldering. This method of construction is relatively time consuming and costly in manufacture. Further, the solder attachment of the coil to the guidewire tip may crack during use, presenting the danger of having the coil separate from the wire within a vessel in the patient. Another limitation of the prior art construction is that the distal end section of the wire tends to kink on bending if the coil loses its relatively tight pitch, e.g., by being irreversibly stretched during use.

DISCLOSURE OF THE INVENTION

It is a general object of the invention to provide a guidewire which overcomes limitations or reduces above-noted problems associated with prior art flexible tip guidewires.

The guidewire of the invention includes an elongate wire having a proximal section and a flexible distal end section which is at least about 3 cm long. The distal end section is encased in an elongate polymeric sleeve having, along the length of the sleeve, (a) a continuous polymer expanse, and (b) axially spaced grooves which are effective to increase the bending flexibility of the sleeve and encased distal end section in substantially any bending direction, over the bending flexibility in the absence of the groove.

The sleeve may have inner and outer sleeve portions formed of polymer materials having different flexibilities, such as a low-density polyethylene or latex forming the inner sleeve portion, and a Teflon™, high-density polyethylene, or polyurethane forming the outer sleeve portion. Alternatively, or in addition, the polymer material forming the sleeve may have a relatively greater flexibility progressing in a proximal-to-distal direction.

The grooves or helical groove formed in the outer sleeve portion may be dimensioned to provide greater flexibility on progressing toward the distal end of the sleeve. This can be accomplished by increasing the radial depth and/or the axial width of the groove(s) on progressing toward the sleeve's distal end.

In another aspect, the invention includes a method of increasing the column strength in the tapered, reduced-diameter distal end section of a catheter guidewire. The method includes encasing the end section in an elongate polymeric sleeve having, along the length of the sleeve, (a) a continuous polymer expanse, and (b) axially spaced grooves which are effective to increase the bending flexibility of the sleeve and encased distal end section in substantially any bending direction, over the bending flexibility in the absence of the groove.

Also disclosed is a catheter apparatus composed of the guide wire and a thin-walled catheter designed to be advanced along the guidewire through a tortuous vessel path, for positioning at a target site.

DETAILED DESCRIPTION OF THE INVENTION

A. Guidewire Construction

Figure 1:
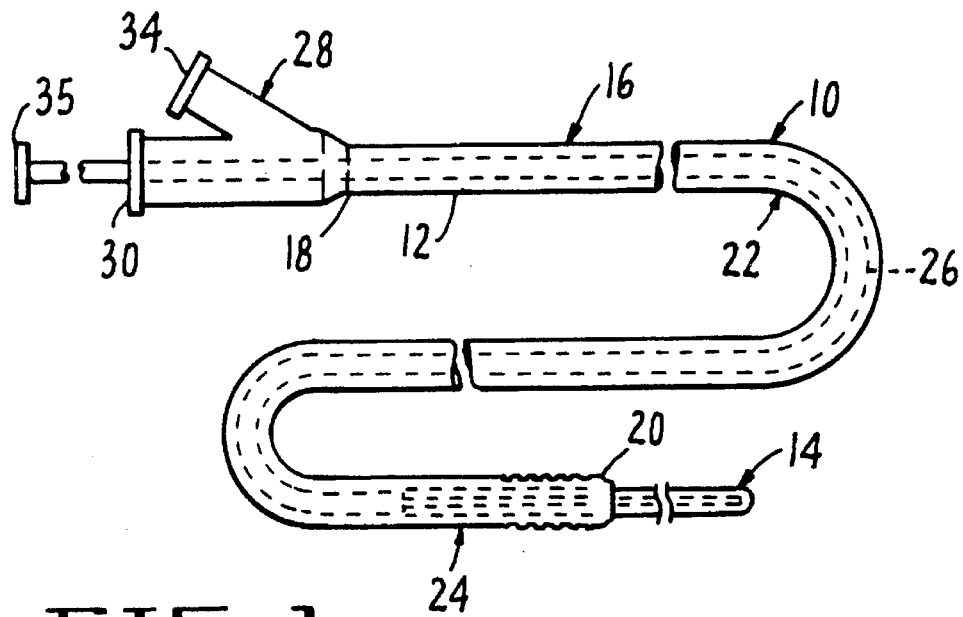
FIG. 1 shows a catheter apparatus, including a flexible-tip guidewire constructed according to the present invention.

FIG. 1 shows a catheter device or apparatus 10 designed for accessing an internal target site in a body along a tortuous vessel path. The device generally includes a catheter 12 and a guidewire 14 constructed according to the present invention, as detailed below.

With continued reference to FIG. 1, the catheter is composed of an elongate tubular member 16 having proximal and distal ends 18, 20, respectively. The tubular member is preferably between about 50–300 cm in length, typically between about 100–200 cm in length. The tubular member is preferably composed of a relatively stiff proximal section, indicated at 22, which extends along a major portion of the catheter length, and one or more relatively flexible distal sections, such as section 24, which provide greater ability of the catheter to track the guidewire through sharp bends and turns which may be encountered as the catheter is advanced along a tortuous path. The construction of a catheter having differential flexibility along its length is described in U.S. Pat. No. 4,739,768.

An inner lumen 26, indicated by the dashed lines, extends between the two ends of the catheter. The lumen may have a substantially uniform cross-sectional area along its length, or may vary along the catheter length, for example, in a distal end taper. It will be appreciated that the tapered construction may require a similar taper in the diameter of the guidewire, to maintain suitable clearance between the guidewire and catheter.

The catheter has an end fitting 28 through which the guidewire is received, and through which fluid material can be introduced into the catheter lumen. One standard fitting which is suitable has an axially extending port 30 through which the guidewire can be received and rotated (torqued) and advanced or retracted axially within the catheter, during a catheter placement operation. An external port 34 may be used to deliver fluid material through the catheter at the target site, after removal of the guidewire.

Figure 2:
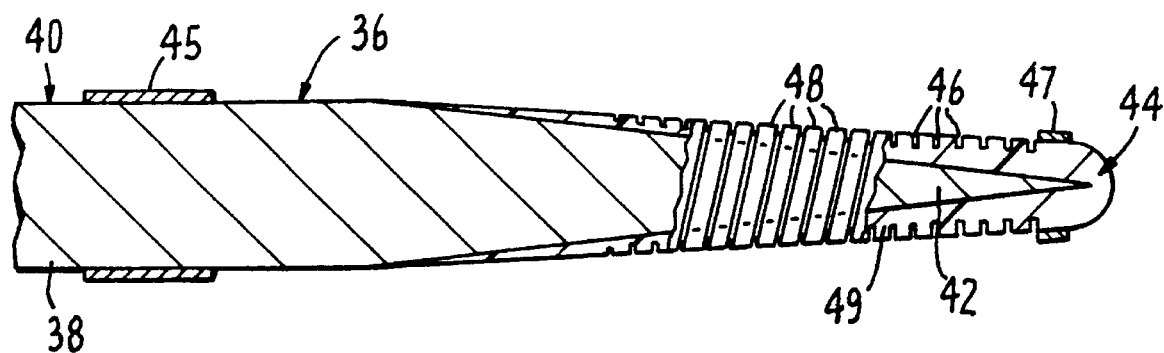
FIG. 2 is an enlarged fragmentary distal-end portion, shown partially in sectional view, of an embodiment of the guidewire of the invention having a helical groove formed in the outer sleeve portion of the guidewire.

FIG. 2 shows an enlarged, partially cross-sectional view of a distal end section of a guidewire 36 constructed according to one embodiment of the present invention. The wire includes an elongate wire core 38 having a relatively stiff proximal section 40 which extends along a major portion of the guidewire, and a more flexible distal section 42 which is preferably tapered along its length as shown.

The wire core is formed of a flexible, torqueable wire filament material, such as stainless steel, and has a total length typically between about 50–300 cm. The proximal section 40 preferably has a uniform diameter thickness along its length of between about 8–30 mils (thousandths of an inch). The relatively more flexible section extends along the distal 3–30 cm or more of the wire core. The taper in the core wire may be continuous, as shown, or stepwise over one or more reduced diameter steps. The minimum diameter of the core at its distal end is preferably between about 1–5 mils.

In one embodiment, the distal end portion of the wire core is coated with a gold or other radio-opaque plating material, to allow this portion of the wire to be visualized by fluoroscopy. The plating may be applied by electroplating, sputtering, or other metal plating methods. The thickness of the plating is preferably between about 0.2 to 0.5 mils.

The distal region of the wire core, i.e., at least about a 3-cm distal end section of the core, is encased in an elongate polymeric sleeve 40. The length of the sleeve is preferably about 3–25 cm, and the wall thickness is preferably between about 2–10 mils.

The material forming the sleeve includes at least an inner or outer sleeve portion which is relatively non-elastic under axial compression or extension. Preferred polymers include Teflon™, a high-density polyolefin (e.g., polyethylene), or polyurethane which can be bonded or otherwise tightly affixed to the core wire, and which itself has a low-friction surface, as is the case for Teflon™, or whose surface can be coated with a low-friction surface. Other suitable coatings include virtually any polymer having exposed hydrogens, such as polyester, polycarbonate, polyvinylchloride, latex or silicone rubber, polystyrene, and a surface coating formed of a highly hydrophilic, low-friction polymer such as polyvinylpyrrolidone, polyethyleneoxide, or polyhydroxyethylmethacrylate or copolymers thereof.

The sleeve can be formed conventionally, such as by extrusion, or molding, dip coating. In the former case, the extruded sleeve can be attached to the wire core by friction fit, adhesives, or heat-shrinkage. In the case of a molded sleeve, the polymer material is preferably molded directly on the distal end region of the wire core. The sleeve-encased portion of the wire may be surface roughened, such as by chemical treatment, prior to molding. Forming the sleeve by dip coating is done by successive dipping of the core distal region in a suitable polymer solution, according to conventional methods of polymer coat build-up. As will be seen below, the sleeve may be composed of two or more different polymer materials which differ in flexibility along either the axis or radial dimension of the sleeve.

With continued reference to FIG. 2, sleeve 44 has a helical groove 46 (referred to hereinbelow as axially spaced grooves or groove means) extending along a major portion of its length. The grooves, which can be formed according to the method described below with reference to FIG. 8, have a uniform depth and helical pitch substantially along the length of the sleeve. The depth of the grooves is preferably at least about 50% percent of the average radial dimension of the sleeve. The pitch of the groove is preferably about 5–50 mils. The width of the grooves is preferably about 10–40% of the width of the pitch, e.g., 2–10 mils. The grooves in the sleeve form helical strands or windings 48 which are formed integrally with and encircle an inner portion 49 of the sleeve. In the embodiment shown in FIG. 2, the groove is formed by cutting with a blade, as described in Section B below.

The guidewire is provided with a pair of radio-opaque bands 45, 47 located adjacent opposite ends of the sleeve, as shown, for use in visualizing the guidewire fluoroscopically (if the distal section of the wire core is not plated with a radio-opaque material). The sleeve portion of the bands is formed of gold, platinum or the like and clamped to the guidewire.

Figure 3:
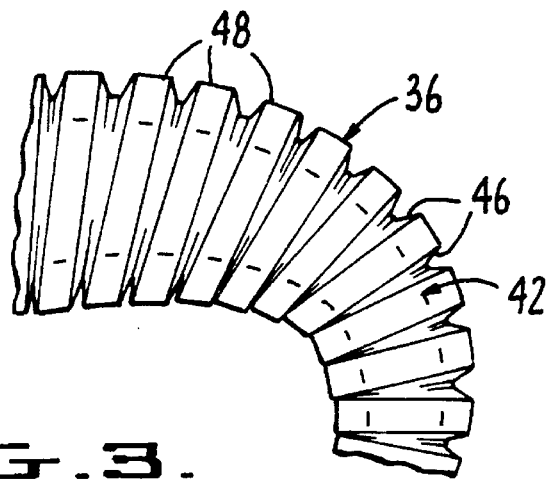
FIG. 3 illustrates how the grooves in the outer sleeve portion of the guidewire, such as the FIG. 3 guidewire, accommodate bending.

FIG. 3 shows the distal end region of the FIG. 2 wire in a bent configuration, illustrating how the helical grooves in the sleeve contribute to greater flexibility in the distal end of the guidewire. It is known that the force required for bending a tube is related to the wall thickness of the tube, the tube's outer diameter, and the bending modulus of the material forming the tube. In the present case, the helical windings in the outer portion of the sleeve effectively reduce the outer diameter of the outer portion of the sleeve by the depth of the groove, typically greater than half the sleeve wall thickness. This substantially reduces the effective bending modulus of the material (by reducing the thickness of the wall which undergoes bending). On the inner side of the arc, the windings can accommodate bending by a slight radial displacement, as indicated, also reducing the effective bending modulus by reducing the radius of the inner wall of the tube.

Also as seen in FIG. 3, when the guidewire is in a bent condition, the helical windings on the inner side of the bending arc are brought into contact with one another, and at a sufficient bending angle, become compressed against one another. This contact and compression increases the effective cross sectional thickness and resistance to axial compression in the guidewire, thus increasing the column strength of the guidewire in the region of the bend.

Also, the radial sliding movement of the windings under compression, noted above, relieves localized compression in the region of the turn, and thus reduces the tendency of the wire to buckle under axial compression in a region of sharp turn.

Figure 4:
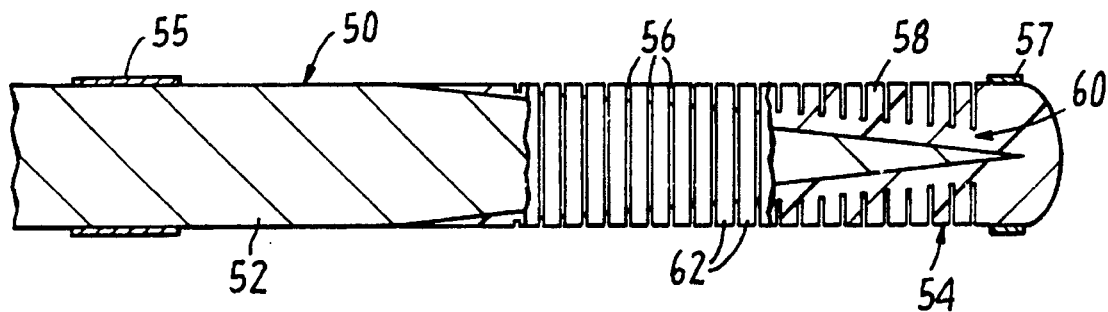
FIG. 4 is a view like that in FIG. 2, illustrating an embodiment of the guidewire having formed in the outer sleeve portion of the wire, a series of axially spaced grooves whose depths increase on progressing toward the distal end of the guidewire.

FIG. 4 shows an enlarged, partially cross sectional view of the distal end region of a guidewire 50 constructed according to another embodiment of the invention. The wire core and polymer sleeve forming the distal end portion of the guidewire are indicated at 52, 54, respectively. The invention differs from the FIG. 2 embodiment in two respects. First, the sleeve, when placed on the tapered portion of the wire core, has a substantially uniform diameter along its length, corresponding approximately to the outer diameter of the core wire. The sleeve can be formed, for example, by molding the sleeve on the tapered end section of the wire core, or by dip coating to produce progressively greater sleeve thickness on progressing toward the distal end of the sleeve.

Secondly, the groove means in the sleeve includes a plurality of axially spaced circumferential grooves, such as grooves 56 extending through an outer portion 58 of the sleeve, with increasing groove depth on progressing toward the distal end of the sleeve. As seen, the depth of the grooves is such as to define a substantially uniform-thickness inner portion 60 extending along the length of the sleeve, in contact with the tapered portion of the core. The depth of the grooves increases from about 10% to about 80% of the radial thickness of the sleeve, on progressing distally. The axial spacing between grooves is similar to the pitch of the helical groove in the FIG. 2 embodiment.

The grooves form a plurality of axially spaced rings, such as rings 62, with uniform outer diameters and decreasing inner diameters progressing distally along the sleeve. The grooves may be formed, for example, by the method described below with reference to FIG. 10. The functioning of the rings to reduce flexibility along the length of the distal portion of the guidewire, and reduce the tendency of the wire to buckle is substantially as described with reference to FIG. 3. In particular, the relatively deeper grooves in the sleeve in the distal direction provide a small, substantially uniform effective wall thickness along the outer arc of the entire sleeve length on bending.

It will be appreciated that the guidewire construction shown in FIG. 4 provides greater column strength than the FIG. 2 construction on bending, due to the greater effective thickness of the sleeve in a bent condition in which the rings of the sleeve are in contact and are compressed against one another along the inner arc of the turn.

Figure 5:
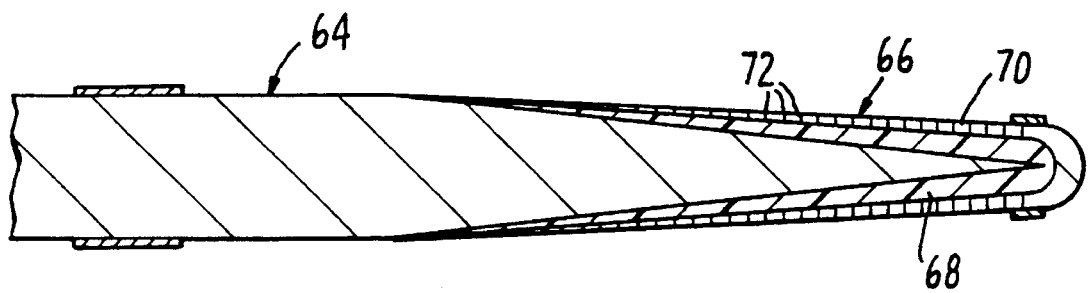
FIG. 5 is a view like FIG. 2, illustrating a guidewire embodiment with a coaxial-sleeve construction.
Figure 6:
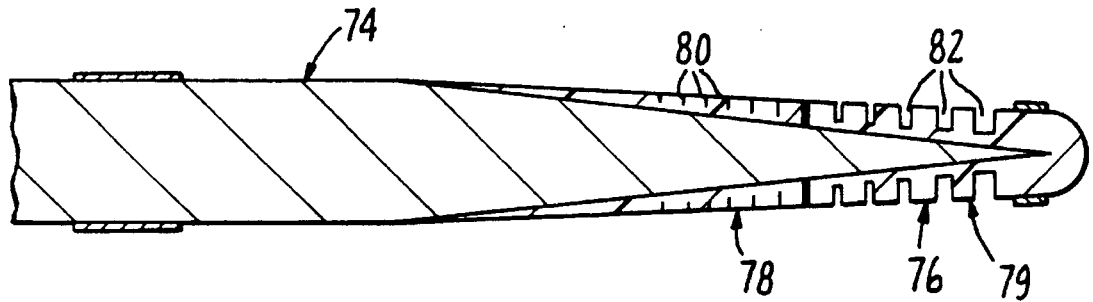
FIG. 6 is a view like FIG. 2, illustrating an embodiment of the invention in which material forming the sleeve in the guidewire has a single-step flexibility gradient along its length.
Figure 7:
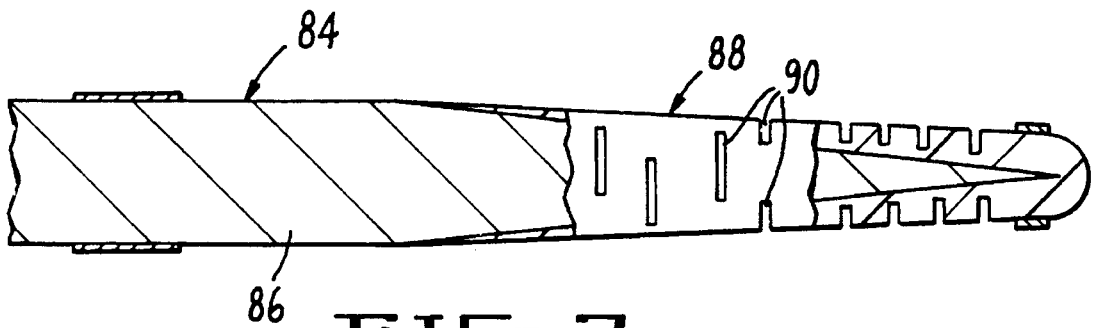
FIG. 7 is a view like FIG. 2, illustrating an embodiment of the invention having a series of axially spaced non-circumferential grooves formed in its outer sleeve portion.

Guidewire 50, as well as the guidewires illustrated in FIGS. 5–7, are provided with radio-opaque bands, such as bands 55, 57 shown in FIG. 4.

FIG. 5 shows an embodiment of a guidewire 64 constructed according to a third embodiment of the invention. Guidewire 64 differs from guidewire 36 shown in FIG. 2 in that the sleeve, here indicated at 66, is composed of an inner, elastomeric tube 68, and an outer, relatively non-elastic tube 70 encasing the inner tube. The two tubes may be formed together by fusing them chemically or by heat, by an adhesive, or by heat shrinking the outer tube over the inner one. Typically the inner tube is formed of latex or other flexible elastomer, and the outer tube, of polypropylene, high-density polyethylene, or Teflon™.

The groove means formed in sleeve 66 includes axially spaced circumferential grooves 72 which extend through outer tube 70 only. Preferably the width of the grooves is sufficiently small, e.g., less than about a mil, so that the rings formed by the grooves in the outer portion of the sleeve are in contact with one another in the straight condition of the wire.

The column flexibility of the distal end portion of the wire is provided by the elastomeric inner sleeve portion, which allows the relatively incompressible rings formed in the outer sleeve portion to spread apart in the outer arc of a bend. That is, the resistance to bending contributed by the sleeve is the resistance of the elastomeric sleeve itself to bending plus the distortion in the elastomeric sleeve produced by the spreading apart of the rings in the outer arc of the bend. It can be appreciated that this resistance can be made quite small.

At the same time, the stacking of the rings against one another, either in a straight- or bent-wire configuration adds significantly to the column strength of the wire's distal end region, since compressing the rings in an axial direction requires an axial distortion along the entire length of the sleeve.

Another embodiment of the invention is shown at 74 in FIG. 6. Here the guidewire sleeve, indicated at 76, is composed of a proximal sleeve section 78 formed of a polymer having a selected flexibility, and a distal sleeve section 80 formed of a more flexible polymer material. By way of example, the proximal and distal sections may be formed of high- and low-density polyethylene, respectively.

The groove means formed in sleeve 76 includes a series of axial grooves, such as grooves 80 in the proximal sleeve section, and grooves 82 formed in the distal sleeve section. As seen, the latter grooves have increasing axial widths on progressing distally, allowing increasing flexibility through this section of the guidewire. This feature is gained at the expense of reduced column strength in the distal section, since the rings formed by the grooves do not support column compression except when the guidewire is bent to bring the rings into contact at the inner arc of the bend. This embodiment further illustrates the ability to selectively vary flexibility and column strength properties along the length of the distal region of the guidewire by varying (a) flexibility of the material forming the sleeve, (b) thickness of the sleeve, and (c) depth and width of the grooves formed in the sleeve.

FIG. 7 shows a guidewire 84 formed in accordance with another embodiment of the invention, and composed of a wire core 86 and a sleeve 88. The groove means in the sleeve includes a plurality of axially spaced grooves, such as grooves 90, which (a) extend about only a portion of the sleeve circumference, (b) are axially misaligned, so that the circumference of the sleeve is not continuously cut at any axial location, and (c) extend a selected depth through the sleeve, and may be through the entire thickness of the sleeve.

The grooves in the guidewire increase the flexibility of the distal end region for the reasons discussed. At the same time, the continuity of sleeve material in an axial direction, which substantially prevents stretching or compression of the sleeve, adds column strength to the wire core.

Figure 8:
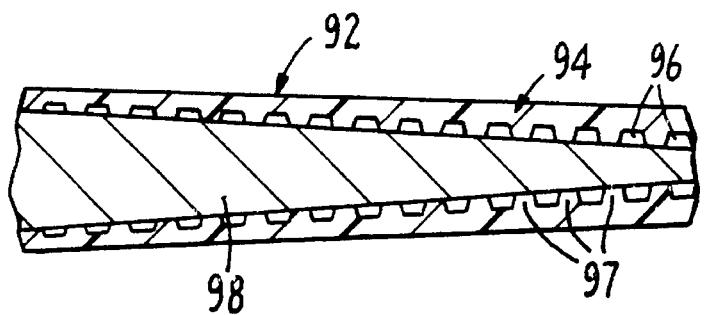
FIG. 8 is a view like FIG. 2, illustrating an embodiment of the invention in which grooves are formed on the inner wall of the sleeve.

Yet another embodiment of the invention is shown at 92 in FIG. 8. A sleeve 94 in this embodiment has inner-surfacegrooves, such as grooves 96, forming a series of inner, axially spaced rings, such as rings 97, which are attached to the wire core, indicated at 98, as by adhesives. The sleeve may be prepared for example by forming an extruded tube about a threaded mandrel, and "unwinding" the mandrel from the tube after hardening.

When the sleeve portion of the guide wire is bent, the inner rings of the sleeve accommodate bending by localized deformation due to compression or stretching in a radial direction. This has the effect of reducing the effective bending modulus of the sleeve by reducing the thickness of the sleeve which undergoes bending. At the same time, the ungrooved outer portion of the sleeve contributes to the column strength of the wire in both a straight or bent-wire configuration.

In each of the guidewires described above, the polymer sleeve encasing the wire core includes a sleeve which has (a) a continuous or unbroken polymer expanse, and (b) axially spaced grooves which are effective to increase the bending flexibility of the sleeve. The continuous polymer expanse in the FIG. 2–6 embodiments is the inner, ungrooved sleeve portion which forms a continuous expanse in contact with the wire core; in the FIG. 7 embodiment, the ungrooved portion of the sleeve; and in the FIG. 8 embodiment, the outer, ungrooved portion of the sleeve.

In each embodiment, the continuous polymer expanse provides a relatively incompressible expanse effective to increase the column strength of the encased distal end portion of the wire core (FIGS. 2, 4, and 6–8), or a flexible substrate on which a relatively incompressible grooved portion of the sleeve is mounted, for producing the requisite column strength (FIG. 5).

B. Guidewire Method

In another aspect the invention includes a method of increasing the column strength in the tapered, reduced diameter distal end section of a catheter guidewire wire core. The method includes encasing the distal end section of the core in a polymeric sleeve having (a) a substantially continuous planar expanse along its length, and (b) axially spaced grooves disposed along the length of the sleeve for increasing the bending flexibility of the sleeve and encased distal end section in substantially any bending direction, substantially along the length of the sleeve, over the bending flexibility in the absence of the grooves.

A variety of polymer sleeves suitable for use in practicing the invention have been described in Section A above. The sleeve may be secured to a wire core's distal end region by adhesives,. heat shrinking the sleeve on the wire core, or by chemical bonding to a chemically treated core coated surface. Alternatively, the sleeve may be formed on the wire core by dip coating.

The grooves in the sleeve may be formed before or after attachment of the sleeve to the core wire. In a generally preferred method, the sleeve is attached to the core prior to grooving the sleeve.

Figure 9:
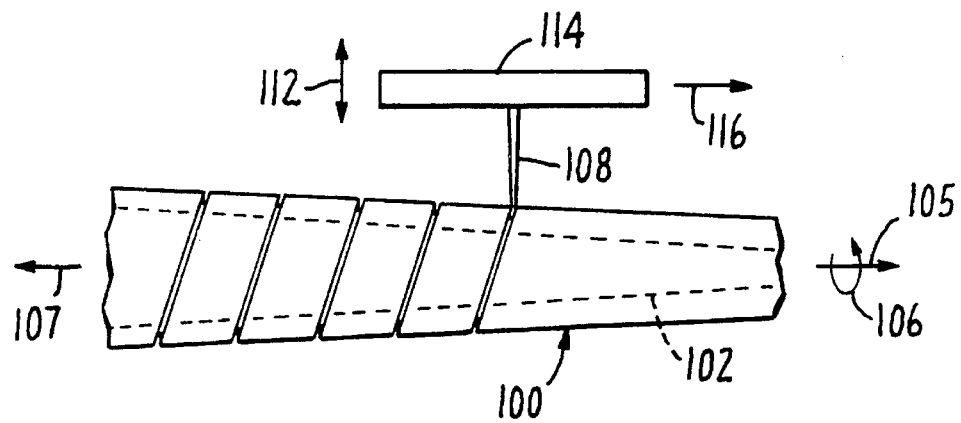
FIG. 9 is a schematic view of a method of producing a guidewire of the type illustrated in FIG. 2.

FIG. 9 illustrates, in schematic view, a method for forming a helical groove in a sleeve 100 encasing a wire core 102. A machine having a pair of motor-driven chucks which are (a) rotated synchronously, and (b) biased under tension away from one another (in the direction of arrows 105, 107) is suitable for use in the FIG. 9 method. The opposite ends of the distal end section of the wire core are supported in the chucks, under tension, and the chucks are rotated at a selected rotational speed, preferably between about 10 and 50 rpm. The direction of rotation is indicated by arrow 106 in the figure.

The sleeve is grooved by a blade 108 which can be positioned (in the direction of arrow 112) a selected distance from the guidewire to a desired depth of cut in the sleeve. The blade, which is also referred to as a cutting tool, is mounted on a carriage 114 for shifting at a selected speed along the axis of the guidewire, as the wire is rotated. The speed of shifting (in the direction of arrow 116) is adjusted to achieve a desired helical pitch in the sleeve. The method of forming a helical groove in a sleeve is suitable for forming the guidewire illustrated in FIG. 2.

Figure 10:
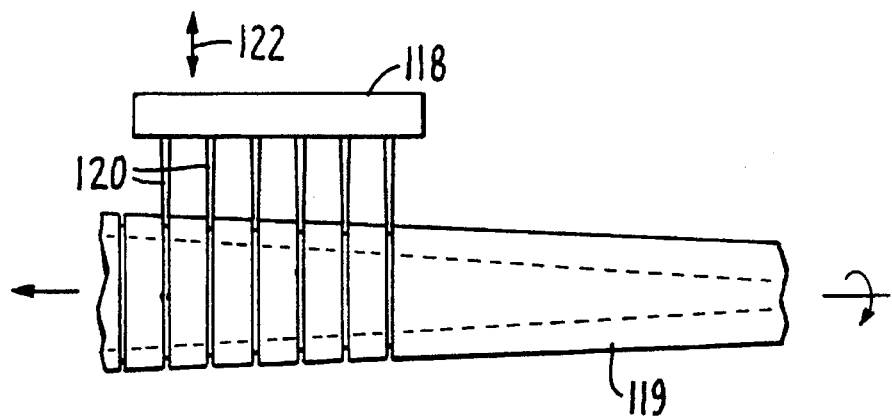
FIG. 10 is a schematic view of a method of producing a guidewire of the type illustrated in FIG. 4.

If a sleeve 119 with an outer portion having axially spaced circumferential grooves of constant depth formed in the sleeve, a cutting configuration like that shown in FIG. 10 can be used. The distal end section of a guide wire is supported in synchronously rotating chucks, as described above. A multiple-blade cutting tool 118 having a plurality of blades, such as blades 120, is mounted adjacent the rotating guidewire for shifting in the direction of arrow 122 to a selected cutting depth in the guide wire sleeve. The cutting tool is preferably moved toward the rotating wire incrementally, such that the maximum groove depth is reached only after several guidewire revolutions. The spacing between adjacent blades is adjusted to produce a desired spacing between adjacent grooves in the sleeve.

Figure 11:
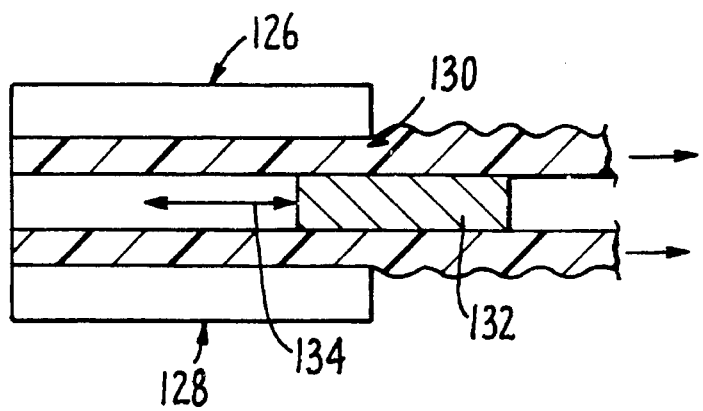
FIG. 11 is a schematic view of a method of producing an extruded polymer sleeve with an accordion outer surface portion.

A method of forming an outer sleeve portion having a bellows-like construction is illustrated in FIG. 11. The figure shows the extrusion tip 126 of a polymer-tube extrusion device 128 having an annulus 130 through which polymer material is extruded in molten form. The tip is modified, in accordance with the present application, to include an oscillatory element 132 which oscillates in the direction of arrow 134 as the polymer material is extruded. This oscillation causes extruded material to be alternately and repeatedly compressed and extended, forming the accordion-like surface feature of the tube which is indicated in the figure. After the tube is formed, it is cut into sections and attached to a guidewire core, e.g., by heat shrinking.

From the foregoing it can be seen how the various objectives of the present invention can be met. The polymeric expanse in the sleeve is effective to give the tapered wire core region of the guidewire added column strength for advancing the wire through a tortuous path vessel region. When the sleeve is bent, compression of the rings or windings in the sleeve provides continued column strength.

The grooves in the sleeve significantly reduce the bending force required to form sharp bends in the distal region of the wire, by (a) effectively reducing the outer diameter of the sleeve on the outer arc of the turn, and (b) accommodating compression on the inner arc of the turn by radial sliding movement. The tendency of the guidewire to buckle in a region of sharp turn is also reduced by the shifting the windings or turns in the inner arc of the turn to reduce localized compression in the sleeve.

The guidewire can be readily formed from inexpensive polymer tube materials, and the composition of the polymer and groove pattern, depth, and axial width can be selected to achieve desired bending and column strength properties along the length of the sleeve portion of the guidewire.

The distal end region of the guidewire can be adapted readily for visualization, e.g., in a fluoroscopic procedure, by radio-opaque bands adjacent opposite ends of the guidewire sleeve.

Although the invention has been described with respect to particular materials and methods, it will be apparent to those skilled in the art that various changes and modification may be made without departing from the invention.

What is claimed is:

1. A method of increasing column strength of a tapered distal end section of a catheter guidewire wire core, comprising:

directly securing to said tapered end section of a catheter guidewire wire core, an elongate polymeric sleeve having axially spaced grooves along the length of the sleeve which grooves are of depth and width so to increase the bending flexibility of the resulting distal end section in substantially any bending direction, along the length of the distal end section, over the bending flexibility in the absence of said grooves and to increase the columnar strength of the tapered distal section, said elongate polymeric sleeve being grooved by the step of extruding the elongate polymeric sleeve under conditions of axial oscillation to produce regular and repeated bunching in the extruded elongate polymeric sleeve so to produce the axially spaced grooves.

2. The method of claim 1, where the elongate polymeric sleeve has a wall thickness and where said grooves have a depth of more than half the wall thickness of said elongate polymeric sleeve.

3. The method of claim 1 where said elongate polymeric sleeve has an inner sleeve portion formed of a relatively soft polymer material, and an outer sleeve portion formed of a relatively rigid polymer material, and where said grooves are in said outer sleeve portion.

* * * * *